United States Patent [19]

Shen et al.

[11] 3,954,852

[45] May 4, 1976

[54] INDENYLACETIC ACID COMPOUNDS

[75] Inventors: Tsung-Ying Shen, Westfield; Howard Jones, Holmdel, both of N.J.

[73] Assignee: Merck & Co., Inc., Rahway, N.J.

[22] Filed: Oct. 19, 1973

[21] Appl. No.: 408,220

[52] U.S. Cl. .................. 260/515 A; 260/240 D; 260/247.1 R; 260/247.2 R; 260/247.2 A; 260/247.2 B; 260/268 BC; 260/293.62; 260/326.5 S; 260/345.7; 260/448 R; 260/465 G; 260/469; 260/470; 260/471 R; 260/472; 260/473 F; 260/479 R; 260/516; 260/518 R; 260/518 A; 260/519; 260/520 D; 260/546; 260/558 S; 260/559 T; 260/578; 260/590; 260/592; 260/599; 260/607 A; 260/609 E; 424/317; 424/319; 424/308; 424/309
[51] Int. Cl.² ............................ C07C 63/595
[58] Field of Search .............. 260/515 A, 470, 516, 260/471 R, 479 R, 473 F, 469

[56] References Cited

UNITED STATES PATENTS

| | | | |
|---|---|---|---|
| 3,312,730 | 4/1967 | Winter et al. | 260/470 |
| 3,609,184 | 9/1971 | Miyai et al. | 260/520 |
| 3,622,623 | 11/1971 | Shen et al. | 260/515 |
| 3,812,180 | 5/1974 | Shen et al. | 260/515 |
| 3,822,310 | 7/1974 | Shen et al. | 260/515 |

*Primary Examiner*—James A. Patten
*Attorney, Agent, or Firm*—Mario A. Monaco; Harry E. Westlake, Jr.

[57] ABSTRACT

4, 5, 6 or 7 Aryl substituted indenyl acetic acids and pharmaceutically acceptable salts, amides and esters thereof. The 4, 5, 6 or 7 aryl substituted indenyl acetic acids have anti-inflammatory, anti-pyretic and analgesic activity. The invention also includes methods for the preparation of these compounds, pharmaceutical compositions and methods of treating inflammation by administering these particular compounds to patients.

4 Claims, No Drawings

INDENYLACETIC ACID COMPOUNDS

SUMMARY OF THE INVENTION

This invention relates to novel 4, 5, 6 or 7 aryl substituted indenyl acetic acids and derivatives thereof, to pharmaceutical compositions, to a method of treating fever, pain and inflammation by employing these benzylidene indenyl acetic acids and to a process for their preparation. The disclosed class of compounds of this invention exhibit anti-inflammatory activity and are effective in the prevention and inhibition of edema and granuloma tissue formation. They also possess a useful degree of anti-pyretic and analgesic activity.

BACKGROUND OF THE INVENTION

There has been much research carried on in the past two decades for development of anti-inflammatory drugs. As a result, a great many new drugs have been synthesized. Most of these have been steroids of the 11-oxygenated pregnane series. These, while highly effective, have the drawback of causing many side effects. There has also been a concentrated effort in anti-inflammatory research in the indole and indene series with the result of many useful drugs. One particularly useful group of indene compounds are those disclosed in U.S. Pat. No. 3,654,349 issued Apr. 4, 1972. These new compounds are related to the 1-benzylidene indenyl acetic acids as described in said U.S. patent. They differ in one substantial respect in that the aryl group is substituted on the 4, 5, 6 or 7-position of the indene moiety. Because of this substantial difference, the compounds of this invention are prepared by different chemical processes.

DESCRIPTION AND PREFERRED EMBODIMENTS

This invention relates to a class of chemical compounds which contain an aryl substituted moiety on the phenyl group of an indenyl acetic acid. The compounds are more specifically described by the following structural formula:

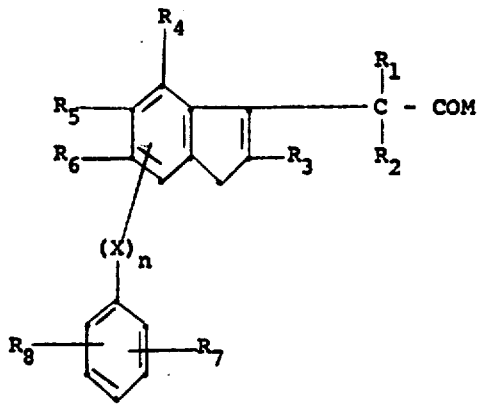

wherein:
$R_1$ and $R_2$ are each hydrogen or alkyl;
$R_3$ is hydrogen, alkyl, halo, haloalkyl, phenyl, alkylthio, phenylthio, alkenyl, alkoxyphenyl, trifluoromethyl or benzyl;
$R_4$, $R_5$ and $R_6$ are each hydrogen, halo, alkyl, alkanoyloxy, alkoxy, acylamino, alkylamino, dialkylamino, dialkylaminoalkyl, sulfamyl, alkythio, mercapto, hydroxy, hydroxyalkyl, alkenyl, alkenyloxy, alkylsulfinyl, alkylsulfonyl, dialkylsulfamyl, carboxyl, carbalkoxy, carbamido, haloalkyl, cycloalkyl, phenyl, benzyl, benzylthio, phenoxy, cycloalkoxy, cyano or alkenyloxy;
$R_7$ is hydrogen, halo, hydroxy, alkoxy, haloalkyl, alkanoylamino or alkanoyl;
$R_8$ is hydrogen, alkylthio, alkylsulfinyl or alkylsulfonyl;
X is $C_{1-5}$ alkylene, alkenylene, alkynylene, -S-, -C=O or NR wherein R is hydrogen, $C_{1-5}$ alkyl or $C_{2-5}$ alkanoyl;
n is 0 or 1;
M is hydroxy, loweralkoxy, loweralkenyloxy, benzyloxy, substituted loweralkoxy, amino, alkylamino, dialkylamino, N-morpholino, hydroxyalkylamino, polyhydroxyalkylamino, dialkylaminoalkylamino, aminoalkylamino, β-D-glucopyranosiduronyl and the group OMe, in which Me is a cation; and their anhydrides.

In the more preferred aspect of this invention: $R_1$, $R_2$, $R_4$ and $R_6$ are each hydrogen;
$R_3$ is hydrogen or $C_{1-5}$ alkyl;
$R_5$ is hydrogen, $C_{2-5}$ alkenyl, halo, $C_{1-5}$ alkoxy, $C_{1-5}$ alkyl, benzyloxy, $C_{1-5}$ alkylthio, $C_{1-5}$ dialkylamino, $C_{2-5}$ alkanoyloxy, $C_{2-5}$ alkenyloxy, $C_{1-5}$ alkylsulfinyl or $C_{1-5}$ alkylsulfonyl;
$R_7$ is hydrogen;
$R_8$ is hydrogen, halo, hydroxy, $C_{1-5}$ alkoxy, $C_{1-5}$ alkylsulfinyl, $C_{1-5}$ alkylsulfonyl, $C_{2-5}$ alkanoyl or $C_{1-5}$ alkylthio;
M is hydroxy, $C_{1-5}$ alkoxy, β-D-glucopyranosiduronyl, NR'R'' wherein R' and R'' are each hydrogen, $C_{1-5}$ alkyl or together form a cyclic amino, (especially hydroxy);
X is $C_{1-5}$ alkylene, alkenylene, alkynylene, -S-, -C=O or NR wherein R is hydrogen, $C_{1-5}$ alkyl or $C_{2-5}$ alkanoyl; and
n is 0 or 1.

Still more particularly, the groups may be defined as follows:
$R_1$, $R_2$, $R_4$ and $R_6$ are each hydrogen;
$R_3$ is $C_{1-5}$ alkyl, especially methyl;
$R_5$ is hydrogen or halo (chloro, bromo, fluoro) especially halo;
$R_7$ is hydrogen;
$R_8$ is hydrogen, $C_{1-5}$ alkylsulfinyl or $C_{1-5}$ alkylsulfonyl (especially $C_{1-5}$ alkylsulfinyl);
M is hydroxy;
n is 0 or 1; and
X is $C_{1-5}$ alkylene, $C_{2-5}$ alkenylene, $C_{2-5}$ alkynylene, -S-, C=O or NR wherein R is hydrogen, $C_{1-5}$ alkyl or $C_{2-5}$ alkanoyl.

The compounds of the instant invention can be used to treat inflammation by reducing inflammation and relieving pain in such diseases as rheumatoid arthritis, osteoarthritis, gout, infectious arthritis and rheumatic fever. The compounds of the invention can also be used as an anti-pyretic and would be administered and used in the same manner and in the same dosage ranges as if they were being used to treat inflammation as discussed further on.

The treatment of inflammation in accordance with the method of the present invention is accomplished by topically, orally, rectally or parenterally administering to patients a composition of a compound of the invention, particularly the especially preferred compounds, in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin, cab-o-sil and acacia. Exemplary of liquid carriers are peanut oil, olive oil, seasame oil and water.

Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, an aqueous solution or a liquid suspension. Suppositories may be prepared in a conventional manner by mixing the compounds of this invention with a suitable non-irritating excipient which is solid at room temperature, but liquid at the rectal temperature. Such materials are cocoa butter and polyethylene glycol. Gels and lotions for topical application may be prepared in conventional manners.

The compounds of this invention are to be administered in an amount sufficient to treat inflammation; that is, to reduce inflammation. Advantageously, the compositions will contain the active ingredient; namely, the compounds of the invention in an amount of from about 0.1 mg. to 50 mg. per kg. body weight per day (5 mg. to 3.5 g. per patient per day), preferably from about 1 mg. to 15 mg. per kg. body weight per day (50 mg. to 1 g. per patient per day).

The method of treatment of this invention comprises administering to a patient (animal or human), a compound of the invention particularly an especially preferred compound admixed with a non-toxic pharmaceutical carrier such as exemplified above. The compounds and particularly the especially preferred compounds will be administered in an amount of from 0.1 mg. to 50 mg. per kg. body weight per day, preferably from about 1 mg. to about 15 mg. per kg. body weight per day. The most rapid and effective anti-inflammatory effect is obtained from oral administration of a daily dosage of from about 1 to 15 mg. per kg. per day. It should be understood, however, that although preferred dosage ranges are given, the dose level for any particular patient depends upon the activity of the specific compound employed. Also, many other factors that modify the actions of drugs will be taken into account by those skilled in the art in the therapeutic use of medicinal agents, for example, age, body weight, sex, diet, time of administration, route of administration, rate of excretion, drug combination, reaction sensitivities and severity of the particular disease.

The ester compounds of this invention may be prepared by reacting an aryl substituted indanone of the following formula with a haloacetate:

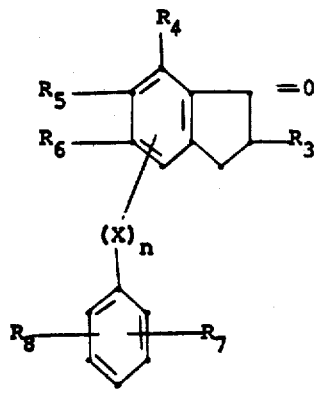

I

The indanone (I) is condensed under Reformatsky conditions. For example, the indanone is reacted with a haloacetate in the presence of zinc dust and iodine, in an inert solvent such as benzene, toluene, ether, tetrahydrofuran or hexane at a temperature of from 0° to 100°C for a period of 6 to 8 hours. Any ester moiety may be used which will give the desired ester group on the product. Preferably, the reaction is carried out with a $C_{1-5}$ alkylbromoacetate (i.e., methyl or ethyl), benzyl or $C_{2-5}$ alkenylbromoacetate in the presence of a solvent such as ether or tetrahydrofuran, at a temperature of from 20° to 40°C for a period of 6 to 18 hours. The concentration of reactants is not critical but preferably there is employed from 2 to 4 moles of haloacetate compound. The product obtained therefrom is then suitably dehydrated with any well known dehydrating reagent such as phosphorous pentoxide, phosphorous pentachloride, ptoluenesulfuric acid or polyphosphoric acid at a temperature of from 50 to 120°C for a period of 1 to 5 hours in the presence of an inert solvent such as benzene, toluene or xylene. The dehydration step, however, is preferably carried out in the presence of polyphosphoric acid as a dehydration agent, benzene as an inert solvent at a temperature of about 80° to 90°C for a period of 0.25 to 2 hours. The quantity of the dehydrating agent is not critical, however, one preferably uses from 10 to 20 moles of dehydrating agent per mole of reactant. The product is obtained in the form of its ester and when the free acids of the invention (M=OH) are desired, the ester is hydrolyzed. The hydrolysis may be carried out using acids or bases under conditions well known to the art for hydrolysis of an ester. Such acids as dilute hydrochloric acid or dilute $H_2SO_4$ at temperatures of from 0° to 120°C may be used as well as organic or inorganic bases such as aqueous or aqueous alcoholic alkali or alkali earth hydroxides, pyridines, alkali or alkali earth carbonate or bicarbonate such as calcium hydroxide, sodium hyroxide, calcium carbonate, sodium carbonate, sodium bicarbonate and the like, but preferably alkali hydroxide (sodium hydroxide, potassium hydroxide) at temperatures of from 0° to 120°C and preferably from 50° to 80°C. Similarly, the concentration of reactants is not critical, however, for the sake of higher yields, one would preferably use between 2 to 6 moles of base or acid to one mole of ester. The reaction may be carried out in a variety of inert solvents, preferably under aqueous or aqueous alcoholic conditions such as aqueous sodium carbonate, sodium hydroxide or mixtures of water and organic bases such as aqueous pyridine or morpholine. The time of reaction is not critical and the reaction is preferably carried out until essentially complete hydrolysis, which usually occurs between 1 to 4 hours.

When one desires the amide compound of this invention (M=NR), the free acid is aminated under conditions well known to the art. For example, the free acid is first converted to its acid halide and subsequently reacted with the appropriate amine. More specifically, the acid is reacted in the presence of a thionyl halide, phosphorous pentachloride, phosphorous oxychloride or sulfinylchloride at temperatures of from 0° to 150°C in the presence, if desired, of an inert solution such as benzene, tetrahydrofuran, dioxan or ether. To this reaction mixture may be then added the desired amine and the mixture further reacted until the amide is formed. The concentration of acid, halogenating compound and amine is not critical and accordingly one may use from 0.1 to 1.0 ml. of acid to 1 ml. halogenating compound and 0.1 to 1.0 ml. of acid to amine.

The various pharmaceutically acceptable salts of the acid may be prepared by normal procedures such as reaction of the acid with an appropriate base or by basic hydrolysis of the ester as previously described. The indanone (I) starting material is prepared from a number of routes as described in the examples.

The following examples are given by way of illustration.

EXAMPLE 1

6-Fluoro-2-methyl-4-(p-methylsulfinylphenyl)-indenyl-1-acetic acid

A. 4-Fluoro-2-nitrotoluene 14 g. of p-fluorotoluene is added slowly with stirring to a solution of 18 gm. fuming nitric acid and 30 gm. of concentrated sulfuric acid over 30 minutes and alternately warmed and cooled to keep the temperature between 40° and 50°C. This is followed by heating at 100°C for 30 minutes more. The organic material is cooled and extracted with methylene chloride to give 16 g. of 4-fluoro-2-nitrotoluene.

B. 4-Fluorotoluidine

The above nitrotoluene is hydrogenated in 200 ml. of ethanol over one teaspoonful of Raney Nickel catalyst with hydrogen at 42 p.s.i. and room temperature. When the theoretical amount of hydrogen has been taken up the hydrogenation is stopped and the catalyst carefully filtered off. The filtrate is evaporated to dryness to yield an oil which is distilled.

C. 4-Chloro-5'-fluoro-2'-methylbiphenyl

The toluidine is diazotized as in reference Cadogan J. Chem. Soc. 4257 (1962), using amyl nitrate and added at 40°C to chlorobenzene as reactant and solvent with a small amount of bright copper powder. The reaction is then stirred at 70°C for 8 hours, poured into dilute hydrochloric acid and extracted with chloroform. The CHCl₃ layer is washed with water, separated, dried (MgSO₄) and filtered. The crude product is put on a column of silica-gel (Baker Analysed 60–200 mesh, 2 ft. × 2 in.). Elution with n-hexane gives pure 4-chloro-5'-fluoro-2'-methylbiphenyl.

D. 4-Chloro-5'-fluoro-2'-formylbiphenyl 67 gm. of bromine is added slowly to a stirred solution of 46.9 gm. of 4-chloro-5'-fluoro-2'-methylbiphenyl wwhile being illuminated. The temperature is kept between 105°–110°C for 1 hour. 120 ml. of water and 90 g. of calcium carbonate is then added to this product with stirring at reflux for 20 hours. The organics are extracted with chloroform (400 ml.) and the chloroform washed with water, separated and dried (MgSO₄). The chloroform solution is evaporated to a solid which is recrystallized from hexane.

E. 5'-Fluoro-2'-formyl-4-methylthiobiphenyl 66 g. of 85% potassium hydroxide solution is dissolved in 700 ml. of ethanol and cooled to room temperature. To this with stirring is added 50 gm. of methyl mercaptan subsurface, 2 ml. of water and a solution of 234.5 gm of 4-chloro-5'-fluoro-2'-formylbiphenyl in 300 ml. of ethanol. A slow stream of methyl mercaptan is continuously fed in while the reaction mixture is held at reflux for 3 hours.

The reaction is poured into water (litre) and the solid filtered off. The solid is recrystallized from benzene.

F. 5'-Fluoro-2'-formyl-4-methylsulfinylbiphenyl

The above product 123 gm. in 1 litre of isopropanol is cooled to 5°C with an ice bath and poured into 220 gm. of 30% hydrogen peroxide and stirred overnight. Excess peroxide is destroyed, the isopropanol stripped off, the product extracted with methylene chloride (6 × 500 ml.) and the organics dried (MgSO₄). The drying agent is filtered off and the solvent evaporated to give 5'-fluoro-2'-formyl-4-methylsulfinylbiphenyl. The solid is recrystallized from benzene.

G. 4-Fluoro-2-(4'-methylsulfinylphenyl)-α-methyl cinnamic acid 262 g. of the last reaction product, 160 gm. of propionic anhydride and 96 gm. of sodium propionate are heated at 135°C for 8 hours. The reaction mixture is poured onto 2 litres of water. The solid precipitate is redissolved on adding 2.5 litres of saturated potassium carbonate. The warm solution is extracted with 2 × 500 ml. of toluene and the aqueous layer carefully acidified with concentrated hydrochloric acid and ice. The solid acid is collected and dried at 100°C over calcium chloride.

H. 4-Fluoro-2-(4'methylsulfinylphenyl) -methylhydro cinnamic acid 300 gm. of the above dried product, 5 gm. of PtO₂ in 3 litres of ethylacetate is hydrogenated at 42 p.s.i. and room temperature until the theoretical uptake of hydrogen has been completed. The catalyst is filtered off and the solvent evaporated to dryness. The crude solid is collected.

I. 6-Fluoro-4-(p-methylsulfinylphenyl)-2-methylindanone 60 gm. of the above dried product is added to 1 kg. of polyphosphoric acid. The mixture is stirred on the steam bath for 4 hours and then poured onto ice-water. The precipitate is collected and dried.

J. Methyl-6-fluoro-2-methyl-4-(p-methylsulfinylphenyl)-idenyl-1-acetate

A mixture of the indanone (30.2 gm.), zinc dust (8.0 gm.), methylbromoacetate (15.2 gm.) in dry benzene (1 litre) is stirred with a crystal of iodine at reflux for 4 to 5 hours. The reaction mixture is poured onto 500 ml. of 5% sulfuric acid, separated and dried (MgSO₄). The filtrate is refluxed with 60 gm. of phosphorous pentoxide with stirring for 2 hours and then decanted. The organic layer is washed with saturated bicarbonate solution and water. After drying and evaporating of the benzene, the ester is recrystallized from benzene.

K. 6-Fluoro2-methyl-4-(p-methylsulfinylphenyl)-indenyl-1-acetic acid

The above ester (10 gm.) is refluxed in 200 ml. of 1:1 ethanol-water containing 4 gm. of sodium hydroxide for 1 hour, cooled and the alcohol evaporated off. extracted with ethyl acetate (2 × 100 ml.) and the aqueous layer acidified with dilute hydrochloric acid. The precipitated solid is filtered off, dried and recrystallized from ethyl acetate.

Similarly when one of the following toluene compounds:

4-chlorotoluene, 4-methoxytoluene,
2-fluorotoluene,
3-fluorotoluene,
toluene,
xylene,
4-dimethylaminotoluene,
4-acetyloxytoluene (except for cyanoacetic acid preparation),
4-vinyltoluene,
4-vinyloxytoluene,
4-methylthiotoluene,
3-methylthiotoluene,
3-benzyloxytoluene or
4-methylsulfinyltoluene is used in place of 4-fluorotoluene in Example 1 A above and the product carried through Examples 1 B-K, there is obtained the corresponding appropriately substituted indenyl-1-acetic acids.

Similarly when benzene,
fluorobenzene,
methylthiobenzene,
hydroxybenzene,
methoxybenzene or
acetylbenzene is used in place of chlorobenzene in Example 1 C and using it also in excess as a solvent and the product carried through Examples 1 D and G-K, there is obtained the corresponding 6-fluoro-2-methyl-4-(substituted phenyl-)-indenyl-1-acetic acid compound.

Similarly when Example 1 is carried out with the omission of Example 1 F, there is obtained 6-fluoro-2-methyl-4-(p-methylthiophenyl)-indenyl-1-acetic acid.

L. Alternate procedure for reaction 1 I

A solution of 6-fluoro-α-methyl-2-(4'-methylsulfinylphenyl) hydrocinnamic acid (64 gm.) in 500 ml. of thionyl chloride is stirred for 90 minutes and then refluxed for 30 minutes. The solution is evaporated to dryness and added in 100 ml. carbon disulfide to a suspension of anhydrous aluminum chloride (60 gm.) in 250 ml. carbon disulfide at < 10° C with stirring. The reaction is stirred at 25° C for 12 hours, poured into 2.1 of 2.5 N hydrochloric acid crushed ice with stirring, ether (1 litre) added and when all has dissolved, the ether is separated and dried (MgSO$_4$). Evaporation of the ether gives the desired indanone.

M. Alternate procedure for reactions 1 J and K combined

A mixture of 6-fluoro-2-methyl-4-(4'-methylsulfinylphenyl indanone) (30.2 gm.), cyanoacetic acid (10.5 gm.), acetic acid (6.6 g.) and ammonium acetate (1.7 gm.) in dry toluene (20 ml.) is refluxed with stirring for 24 hours while the water is removed continuously in a Dean-Stark separator. The toluene is concentrated, the residue dissolved in 200 ml. of 4 N potassium hydroxide solution (100 ml. ethanol, 100 ml. water) and refluxed for 12 hours. The aqueous solution is evaporated to remove the ethanol, filtered and then acidified with concentrated HCl solution. The preceipitated 6-fluoro-2-methyl-4-(p-methylsulfinylphenyl)-indenyl-1-acetic acid is collected and dried at 70° C in the vacuum oven.

EXAMPLE 2

5-Fluoro-2-methyl-7-(p-methylsulfinylstyrryl)-indenyl-3-acetic acid

A. 5-Fluoro-2-nitrotoluene m-Fluorotoluene (1 mole) in concentrated sulfuric acid (200 ml.) is stirred at 0° C while a cold solution of potassium nitrate (1.5 mole) in concentrated sulfuric acid (750 ml.) is added slowly during 3 hours, the temperature being kept below 5° C with an ice-ethanol bath. After the addition is complete, the ice-bath is removed and stirring continued for 3 hours at room temperature.

Water (400 ml.) is added and the organic layer separated, dried (MgSO$_4$) and filtered. The oil is separated by vapor-phase chromatographed on a 200 ×1 cm. silicone oil column (DC 200 20%) on Chromosorb R (60/80) at 191° C and a Helium flow rate of 86 ml./min.

The desired pure nitro-isomer is collected.

B. 5-Fluoro-o-toluidine

5-Fluoro-2-nitrotoluene (0.5 mole) in ethyl acetate (600 ml.) is hydrogenated at 40 p.s.i. of hydrogen over Pd/C catalyst (1) % 2 teaspoons) at room temperature until the theoretical amount of hydrogen has been taken up. The catalyst is filtered off and the solvent evaporated to give the crude oil of 5-fluoro-o-toluidine.

C. 5-Fluoro-o-toluidinylbromide

Bromine (0.5 mole) is added over 1 hour to stirred 5-fluoro-o-toluidine (0.5 mole) at 100° C illuminated with a high wattage lamp. The crude benzyl bromide is used as prepared.

D. 5-Fluoro-o-toluidinyl triphenylphosphonium bromide

The above benzylhalide (0.2 mole) and triphenylphosphine (0.2 mole) are heated at 100° C for 4 hours in dry dimethylformamide. The precipitated phosphonic salt is collected and recrystallized from ethanol.

E. 5-Fluoro-4'-methylsulfinyl-2-amino stilbenes

To a stirred solution of the above salt (0.1 mole) in tetrahydrofuran (200 ml.) at 10° -15° C is added a solution of n-butyl lithium (21.9% in hexane; 0.11 mole) under nitrogen and the stirring continued for 2 hours. To this solution with stirring is then added p-methylsulfinylbenzaldehyde (0.1 mole) in tetrahydrofuran (50 ml.) at 10° C over 20 minutes under nitrogen. Saturated ammonium chloride solution (100 ml.) is run into the reaction after 1 hour at room temperature. The organic layer is separated, dried (MgSO$_4$), filtered and evaporated to yield an oil which is a mixture of cis and trans-5-fluoro-4'-methylsulfinyl-2-amino stilbenes.

These compounds are then separated on the same preparative vapor phase chromatographic column mentioned in Part A above.

F. Cis and trans-5-fluoro-4'-methylsulfinyl-2-cyano stilbenes

A fresh sample of cuprous cyanide is prepared from copper sulphate (65 gm.) in water (205 ml.) sodium bisulfide (18 gm.) in water (52 ml.) and potassium cyanide (18 g.) in water (52 ml.). The precipitated cuprous cyanide is dissolved in a solution of sodium cyanide (26 gm.) in water (65 ml.).

The above aniline (0.5 m.) and sodium nitrite (0.55 m.) in hydrochloric acid, the temperature is kept below 5° C.

The solution of the diazonium chloride is added to the cold solution of the cyanides and the temperature then brought up to between 60–70° C and kept there for 1 hour.

The precipiate is collected, washed well with water and dried. The solid is recrystallized from n-hexane to give the pure cis and trans cyano stilbene isomers.

G. Cis and trans-5-fluoro-4'-methylsulfinyl stilbene-2-aldehydes

The nitrile isomers (0.2 mole) are refluxed in 75% formic acid (1. 5. 1.with Raney nickel (50 g.) at 125° C for 3 hours, evaporated to ¼ volume and the organic aldehydes extracted with methylene chloride solutions.

In this way, the cis and trans stilbene aldehydes are prepared.

H. 5-Fluoro-2-methyl-1-(methylsulfenyldyeryl)-indenyl-3-acetic acid

The compound of Part G above is reacted in the same proportions in accordance with Steps G-K of Example 1 to yield 5-fluoro-2-methyl-1-(p-methyl-sulfinylstyrryl)-indenyl-3-acetic acid.

Similarly when
m-chlorotoluene,
m-dimethylaminotoluene,
m-acetyloxytoluene,
m-vinyltoluene,
m-vinyloxytoluene,
p-methoxytoluene
o-chlorotoluene,
toluene,
m-methylthiotoluene,
p-benzyloxytoluene,
o-xylene or m-methylsulfinyltoluene
is used in place of m-fluorotoluene in Example 2 A above and the product reacted in accordance with Example 2 B-H, there is obtained the corresponding substituted 4-(p-methylsulfinyl styrryl)-indenyl-3-acetic acid.

Similarly when Example 2 is carried out using
p-methylthiobenzaldehyde,
p-hydroxybenzaldehyde,
m-methoxybenzaldehyde,
benzaldehyde,
p-fluorobenzaldehyde,
o-chlorobenzaldehyde,
p-acetylaminobenzaldehyde,
p-acetylbenzaldehyde or
o-methylbenzaldehyde
in place of p-methylsulfinylbenzaldehyde in Example 2 E, there is obtained the corresponding 5-fluoro-2-methyl-4-(substituted styrryl)-indenyl-3-acetic acid.

EXAMPLE 3

5-Fluoro-2-methyl-7-(p-methylsulfinylbenzoyl)-indenyl-3-acetic acid

A. 5-Fluoro-2-methyl-4'-methylsulfinylbenzophenone p-Methylsulfinylbenzoyl chloride (0.2 mole) and p-fluorotoluene (0.2 mole) are refluxed together in trifluoromethanesulfonic acid for 6 hours according to the procedure of Chodroff and Klein, J.A.C.S. 70, 7209 (1948).

In this way, 5-fluoro-2-methyl-4'-methylsulfinylbenzophenone is made and isolated.

B. 4-Fluoro-2-(p-methylsulfinylbenzoyl)benzal bromide

The procedure of Example 2 C is carried out using an equivalent amount of 5-fluoro-2-methyl-4'-methylsulfinylbenzophenone in place of 5-fluoro-o-toluidine and 1.0 mole of bromine to obtain the above compound.

C. 4-Fluoro-2-(p-methylsulfinylbenzoyl) benzaldehyde

The benzal bromide prepared above is refluxed for 20 hours with calcium carbonate (90 g.) in water (120 ml.). The reaction mixture is then steam distilled and the oil distillate dried (Magnesium sulfate). Evaporation of the solvent yields crude aldehyde which is recrystallized from benzene.

D. 5-Fluoro-2-methyl-7-(p-methylsulfinylbenzoyl)-indenyl-3-acetic acid

The procedure of Example 1 G is used employing an equivalent amount of 4-fluoro-2-(p-methylsulfinyl-benzoyl) benzaldehyde in place of 5'-fluoro-2'-formyl-4-methylsulfinylbiphenyl and the product therefrom reacted in accordance with Example 1, Steps H-K to obtain 5-fluoro-2-methyl-4-(p-methylsulfinylbenzoyl)-indenyl-3-acetic acid.

Similarly when an equivalent amount off
p-methylthiobenzoylchloride,
p-hydroxybenzoylchloride,
m-methoxybenzoylchloride,
p-fluorobenzoylchloride,
o-chlorobenzoylchloride,
p-acetylaminobenzoylchloride,
p-acetylbenzoylchloride or
o-methylbenzoylchloride is used in place of p-methylsulfinylbenzoyl chloride in Example 3 A above and the product reacted in accordance with Example 3, Steps B-D, there is obtained the corresponding 5-fluoro-2-methyl-4-(substituted benzoyl)-indenyl-3-acetic acid.

Similarly when an equivalent amount of
4-chlorotoluene,
4-methoxytoluene,
2-fluorotoluene,
3-fluorotoluene,
toluene,
xylene,
4-dimethylaminotoluene,
4-acetyloxytoluene,
4-vinyltoluene,
4-vinyloxytoluene,
4-methylthiotoluene,
3-methylthiotoluene,
3-benzyloxytoluene,
4-methylsulfinyltoluene or
2-methylthiotoluene
is used in place of p-fluorotoluene in Example 3 A above and the product reacted in accordance with Example 3, Steps B-D, there is obtained the corresponding substituted 4-(p-methylsulfinylbenzoyl)-indenyl-3-acetic acid.

EXAMPLE 4

5-Fluoro-2-methyl-7-(p-methylsulfinylphenethynyl)-indenyl-3-acetic acid

A. 5-Fluoro-4'-methylsulfinyl-2-amino-diphenylacetylene

To the product from Example 2 E (0.1 mole) in chloroform (200 ml.) is added bromine (0.2 mole) dropwise over 2 hours at 0°C. The solvent is evaporated off and the product refluxed in 10% sodium ethoxide in ethanol (400 ml.) under nitrogen overnight. The product is evaporated to dryness and extracted with ethyl acetate (4 × 200 ml.). The ethyl acetate is distilled off and the residue fractionally distilled to give pure 5-fluoro-4'-methylsulfinyl-2-amino diphenyl acetylene.

B. 5-Fluoro-2-methyl-7-(p-methylsulfinylphenethynyl)-indenyl-3-acetic acid

An equivalent amount of the product of Example 4 A is used in place of 5-fluoro-4'-methylsulfinyl-2-aminostilbene in Example 2 F above and the product therefrom reacted in accordance with Example 2, G-H, there is obtained 5-fluoro-2-methyl-7-(p-methylsulfinylphenethynyl)-indenyl-3-acetic acid.

Similarly when the other 2-aminostilbenes obtained from Example 2 are used in place of 5-fluoro-4'-methylsulfinyl-2-aminostilbene in Example 4 A above and the product therefrom reacted in accordance with Example 4 B, there is obtained the appropriately substituted 7-phenylpropargyl-indenyl-3-acetic acids.

EXAMPLE 5

5-Fluoro-2-methyl-7-(p-methylsulfinylphenylethyl)-indene-3-acetic acid

A. 5-Fluoro-4'-methylsulfinyl-2-aminodiphenyl ethane

The product from Example 2 E, cis or trans-5-fluoro-4'-methylsulfinyl-2-aminostilbene (0.2 mole) is hydrogenated over Pd/C 10% (2 gm.) in ethyl acetate (500 ml) at 40 p.s.i. of $H_2$ and room temperature until the theoretical amount of $H_2$ has been consumed. The catalyst is filtered off and the solvent evaporated to dryness.

B. 5-Fluoro-2-methyl-7-(p-methylsulfinylphenylethyl)-indene-3-acetic acid

The product obtained from Example 5 A above is reacted in accordance with Example 2 F-H. There is obtained the subject compound.

Similarly when the other 2-aminostilbenes obtained from Example 2 are used in place of 5-fluoro-4'-methylsulfinyl-2-aminostilbene in Example 5 A above and the product therefrom reacted in accordance with Example 5 B, there is obtained the appropriately substituted 7-phenylethyl-indene-3-acetic acids.

EXAMPLE 6

5-Fluoro-2-methyl-7-(p-methylsulfinylbenzyl)-indenyl-3-acetic acid

A. 5-Fluoro-4-methylsulfinyl-2-methyldiphenyl methane

The product from Example 3 A, 5-fluoro-2-methyl-4'-methylsulfinylbenzophenone (0.2 mole), is refluxed in concentrated hydrochloric acid (100 ml.) with zinc amalgam (45 gm.) and water (30 ml.). Hydrogen chloride gas is slowly bubbled in during the reaction. After 2 to 3 hours, the gas supply is stopped and the product steam distilled. The oily distillate is extracted into ether (3 × 300 ml.), washed with water (2 × 50 ml.), dried (MgSO$_4$), filtered and collected by evaporating off the solvent. It is then fractionally distilled under reduced pressure to give pure diphenylmethane.

B. 5-Fluoro-2-methyl-7-(p-methylsulfinylbenzyl)-indenyl-3-acetic acid

The product of Example 6 A is reacted in accordance with the procedure of Example 3 B-D to yield the desired product.

Similarly when the other substituted 4'-methylsulfinylbenzophenones or 5-fluoro-2-methyl-4'-substituted benzophenones obtained from Example 3 are used in place of 5-fluoro-2-methyl-4'-methylsulfinylbenzophenone in Example 6 above, there is obtained the corresponding substituted-7-(p-methylsulfinylbenzyl)-indenyl-3-acetic acid and 5-fluoro-2-methyl-7-(substituted benzyl)-indenyl-3-acetic acid, respectively.

EXAMPLE 7

N-acetyl-5-fluoro-2-methyl-7-(p-methylsulfinylanilino)-indenyl-3-acetic acid

A. 5-Fluoro-4'-methylsulfinyl-2-nitrobiphenylamine

2-Iodo-4-fluoronitrobenzene (0.2 mole) and p-methylsulfinylaniline (0.2 mole) are refluxed in dry dimethylformamide (300 ml.) containing copper powder (5 gm.) and some powdered potassium carbonate (20 gm.) under nitrogen for 18 hours. The solution is filtered and the organics washed with water (6 × 100 ml.) in benzene (600 ml.). The benzene layer is extracted with 2.5 N HCl (7 × 200 ml.) and the acid layer poured onto powdered sodium bicarbonate. The basic solution is extracted with benzene (6 × 200 ml.), the benzene layer washed with water (3 × 100 ml.), separated, dried (MgSO$_4$) and filtered. Evaporation of the solvent followed by chromatography on a 2 in. × 24 in. column of silica-gel (Baker) eluted with various proportions of benzene-hexane mixtures gives pure 5-fluoro-4'-methylsulfinyl-2-nitrobiphenylamine.

B. N-acetyl-5-fluoro-4'-methylsulfinyl-2-nitrobiphenylamine

The above compound (0.5 mole) is stirred overnight at room temperature in pyridine (200 ml., with acetic anhydride (0.55 mole). The solution is evaporated to dryness at 5°C, dissolved in dichloromethane (600 ml.) and extracted with 2.5 N hydrochloric acid (6 × 200 ml.), water (12 × 100 ml.) and the dichloromethane layer dried (MgSO$_4$). Filtering and evaporating to dryness gives N-acetyl-5-fluoro-4'-methylsulfinyl-2-nitrobipphenylamine.

C. N-acetyl-5-fluoro-2-methyl-7-(p-methylsulfinylanilino)-indenyl-3-acetic acid

The compound from Example 7 B above is reduced in accordance with the procedure of Example 2 B to yield the corresponding amino compound. This compound in turn is reacted in accordance with the procedure of Example 2 F to form the corresponding cyano compound and further reacted in accordance with the procedure of Example 2 G and H to form the desired N-acetyl 5-fluoro-2-methyl-7-(p-methylsulfinylanilino)-indenyl-3-acetic acid.

Similarly when
p-chloroaniline,
p-methylaniline,
o-methoxyaniline,
p-methylthioaniline or
p-methylsulfonylaniline
is used in place of p-methylsulfinylaniline in Example 7 A above and the product therefrom carried through Example 7 C, there is obtained the corresponding N-acetyl-5-fluoro-2-methyl-7-(substituted anilino)-indenyl-3-acetic acid.

Similarly when
2-iodo-4-chloronitrobenzene,
2-iodo-4-methoxynitrobenzene,
2-iodo-4-methylnitrobenzene or
2-iodo-3-methylnitrobenzene
is used in place of 2-iodo-4-fluoronitrobenzene in Example 7 A above and the product therefrom reacted in accordance with Example 7 B-C, there is obtained the corresponding N-acetyl-4 or 5 substituted-2-methyl-7-(p-methylsulfinylanilino)-indenyl-3-acetic acid.

EXAMPLE 8

5-Fluoro-2-methyl-1-(p-methylsulfinylanilino)-indenyl-3-acetic acid

The product from Example 7 above (0.1 mole) in ethanol (120 ml.) and concentrated hydrochloric acid (100 ml.) is refluxed and stirred for 4 hours. Ethyl acetate and ethanol are removed on the rotorary evaporator and the solution poured into solid sodium bicarbonate. The solution is back acidified to slightly acid pH with glacial acetic acid and the precipitated acid filtered off, dried and recrystallized from ethyl acetate.

EXAMPLE 9

N-methyl-5-fluoro-2-methyl-7-(p-methylsulfinylanilino)-indenyl-3-acetic acid

A. N-methyl-5-fluoro-4'-methylsulfinyl-2-nitrobiphenylamine

The product from Example 7 A (0.1 mole), aqueous formaldehyde (37% 0.11 mole) and formic acid (80% 0.11 mole) are refluxed for 4 hours and the tertiary amine extracted with chloroform (2 × 75 ml.). The chloroform solution is dried (MgSO$_4$), the organic solution filtered and evaporated to give N-methyl-5-fluoro-4'-methylsulfinyl-2-nitrobiphenylamine.

B. N-methyl-5-fluoro-2-methyl-7-(p-methylsulfinylanilino)-indenyl-3-acetic acid

The reaction of Example 7 B through to the end is carried out on the above compound, Example 8 A, to give N-methyl-5-fluoro-2-methyl-7-(p-methylsulfinylanilino)-indenyl-3-acetic acid.

EXAMPLE 10

5-Fluoro-2-methyl-7-(p-methylsulfinylphenylthio)-indenyl-3-acetic acid

A. 5-Fluoro-4'-methylsulfinyl-2-nitrobiphenyl sulfide p-Methylsulfinylthiophenol 0.2 mole) is dissolved in dry tetrahydrofuran (100 ml.) and sodium hydride (50% dispersion in mineral oil, 0.2 mole) is added over 30 minutes. The solution is evaporated to dryness and the residue rinsed well with n-hexane. The powdered salt is stirred under N$_2$ at reflux with 4-fluoro-2-iodonitrobenzene (0.2 mole) in dry dimethylformamide for 16 hours, evaporated to dryness and extracted into chloroform (3 × 200 ml.). The organics are washed with water (2 × 100 ml.), separated and dried (MgSO$_4$). The solution is filtered, evaporated to dryness and put on a column of silica-gel (Baker 2 in. × 2 ft.) and various fractions eluted with portions of benzene-n-hexane. In this way, pure 5-fluoro-4'-methylsulfinyl-2-nitrobiphenyl sulfide is obtained.

B. 4-Fluoro-2-(p-methylsulfinylphenylthio)-aniline

The reaction described in Example 2 B is repeated on the product of Example 10 A above to give the title compound.

C. 2-Cyano-5-fluoro-4'-methylsulfinylbiphenyl sulfide

The reaction described in Example 2 F is repeated on the product above to give the title compound.

D. 4-Fluoro-2-(p-methylsulfinylphenylthio)benzaldehyde

The reaction described in Example 2 G is repeated on the above product to give the title compound.

E. 5-Fluoro-2-methyl-7-(p-methylsulfinylphenylthio)-indenyl-3-acetic acid

The product from Example 10 D is reacted in accordance with the procedure of Example 2 H to yield the desired compound.

Similarly when
p-methylthiothiophenol,
p-methylthiophenol,
p-methoxythiophenol or
p-chlorothiophenol
is used in place of p-methylsulfinylthiophenol in Example 10 A above and the product carried through the reaction of Example 10 B-E, there is obtained the appropriate 5-fluoro-2-methyl-7-(substituted phenylthio)-indenyl-3-acetic acids.

Similarly when
4-methoxy-2-iodo-nitrobenzene,
4-methyl-2-iodo-nitrobenzene, or
4-chloro-2-iodo-nitrobenzene
is used in place of 4-fluoro-2-iodo-nitrobenzene in Example 10 A above and the product reacted in accordance with Example 10 B-E, there is obtained the corresponding 5-substituted 2-methyl-7-(p-methylsulfinylphenylthio)-indenyl-3-acetic acid.

EXAMPLE 11

6-Fluoro-2-methyl-4-(p-methylsulfinylphenyl)-indenyl-1-aceto-β-D-glucopyranosiduronic acid Sodium methoxide (25% solution, 30 ml.) is added to a stirred solution of 6-fluoro-2-methyl-4-(p-methylsulfinylphenyl)-indenyl-1-acetic acid (0.13 M) in tetrahydrofuran (800 ml.). The precipitate is filtered off and dried at 60°C under vacuum.

Methyl (tri-O-acetyl-α-D-glucopyranosylbromide)-uronate is made according to a procedure described in J. Amer. Chem. Soc. 77 3310 (1955) or J. Amer. Chem. Soc. 82 2827 (1960).

The dry sodium salt (0.1 M) and the bromopyranoside (0.12 M) are heated in dry dimethyl sulfoxide with stirring at 60°C for 2 hours. The product was used as is, the free acid, is a biproduct of the next reaction.

The crude product (13 gm.) in dimethoxyethane (125 ml.) and 2.5 N hydrochloric acid (62.5 ml.) is heated to 90°C for 3 hours. The solution is evaporated at 70°C to ½ volume and extracted with methylene chloride (2 × 30 ml.). The solution is then saturated with sodium chloride and extracted with methylene chloride again (30 ml.). Then ethyl acetate (2 × 50 ml.) and this last extraction washed with water (20 ml.) dried (anhydrous magnesium sulfate), filtered and evaporated to dryness. In this way, the glucuronide is isolated from the starting material.

Using the same reaction procedures and techniques, the glucoronides of the previously mentioned acids are obtained.

EXAMPLE 12

5-Fluoro-2-methyl-7-(p-methylsulfinylstyrryl)-indenyl-3-acetic anhydride

A solution of 0.05 m. of N,N'-dicyclohexyl carbodiimide in 60 ml. of tetrahydrofuran is added to 0.05 m. of 5-fluoro-2-methyl-7-(p-methylsulfinylstyrryl)-indenyl-3-acetic acid in 25 ml. of tetrahydrofuran. The reaction mixture is shaken vigorously at about 25°C for 16 hours. The dicyclohexylureau is filtered off and 2 ml. of glacial acetic acid is added to the filtrate. The solution is allowed to stand for 1 hour, filtered and 200 ml. of ether added to the filtrate. The filtrate is then extracted well with water, dried and concentrated. The desired product is purified by column chromatography on silica gel using ether-petroleum ether as an eluent.

Similarly when other acetic acid compounds previously are used in an equivalent amount in place of 3-fluoro-2-methyl-7-(p-methylsulfinylstyrryl)-3-acetic acid in the above example, there are obtained the corresponding anhydrides.

EXAMPLE 13

5-Fluoro-2-methyl-7-(p-methylsulfinylbenzoyl)-indenyl-3-acetamide

5-Fluoro-2-methyl-7-(p-methylsulfinylbenzoyl)-indenyl-3-acetic acid (0.01 mole) is warmed with thionyl chloride (5 ml.) for 25 minutes. The mixture is cooled to 25°C and poured with stirring into ice-cold concentrated ammonia solution. The precipitated amide is washed with water, dried and recrystallized from methanol-water to yield the subject compound.

Similarly when ammonia is replaced by an equivalent amount of the following amines, the corresponding amides are obtained:
Morpholine,
Dimethylamine,
Ethanolamine,
Benzylamine,
N,N-diethylethylenediamine,
Benzylglycinate,
Piperidine,
Pyrrolidine,
N-methylpiperazine,
N-phenylpiperazine,
N-hydroxyethylpiperazine,
Piperazine,
Diethylamine,
Diethanolamine,
Aniline,
p-Ethoxyaniline,
p-Chloroaniline,
p-Fluoroaniline,
p-Trifluoromethylaniline,
Butylamine,
Cyclohexylamine,
Methylamine,
D-glucosamine,
Tetra-O-acetyl-d-glucosamine,
D-galactosylamine,
D-mannosylamine,
N,N-dimethylglycine amide,
N,N-dibutylglycine amide,
N-methyl-2-aminomethylpiperidine,
N-methyl-2-aminomethylpyrrolidine,
β-Ethoxyethylamine,
Di(β-ethoxyethyl)amine,
β-Phenethylamine,
α-Phenethylamine,
Dibenzylamine or
D-mannosamine Similarly when the other acetic acid compounds are used in place of an equivalent amount of 5-fluoro-2-methyl-4-(p-methylsulfinylbenzoyl)-indenyl-3-acetic acid in the above example, the corresponding amides are formed.

EXAMPLE 14 t-Butyl-5-fluoro-2-methyl-7-(p-methylsulfinylpropargyl)-indenyl-3-acetate

5-Fluoro-2-methyl-7-(p-methylsulfinylpropargly)-indenyl-3-acetic acid (0.01 mole) is added to isobutylene (30 ml.) and concentrated sulfuric acid (0.1 ml.). The mixture is stoppered securely and shaken at 25°C for 18 hours, chilled to 0°C and the whole poured into a separatory funnel containing ether (50 ml.), water (25 ml.), ice (25 ml.) and sodium hydroxide (1.0 g.). The layers are separated, the water layer extracted with ether (2 × 40 ml.), the etheral extracts washed with water and saturated salt solution and dried ($MgSO_4$). The ethereal extract is concentrated to dryness and the residue crystallized from ethyl acetate-n-hexane to yield the subject compound.

EXAMPLE 15

Ammonium 5-fluoro-2-methyl-7-(p-methylsulfinylphenethyl)-indenyl-3-acetate

To 5-fluoro- 2-methyl-7-(p-methylsulfinylphenethyl)-indenyl-3-acetic acid (0.001 mole) in methanol (10 ml.) is added methanolic ammonia (1 N, 1 ml.). The mixture is evaporated to dryness to yield the subject compound.

EXAMPLE 16

Calcium 5-fluoro-2-methyl-7-(p-methylsulfinylphenethyl)-indenyl-3-acetate

To a slurry of 5-fluoro-2-methyl-7-(p-methylsulfinylphenethyl)-indenyl-3-acetic acid (0.002 mole) in water (10 ml.) is added hydrated calcium oxide (0.076 g., 0.001 mole) and the mixture stirred for 15 minutes. The mixture is concentrated to dryness in vacuo, slurried with methanol (10 ml.) and again concentrated to dryness to yield the subject compound.

EXAMPLE 17

Aluminum 5-fluoro-2-methyl-7-(p-methylsulfinylphenethyl)-indenyl-3-acetate

To a solution of aluminum tert-butoxide (0.246 g., 0.001 mole) in ether (50 ml.) is added 3-cyano-1-methyl-5-(p-methylsulfinylbenzylidene cyclopentadienyl)-2-acetic acid (0.003 mole) in pyridine (50 ml.) with stirring at 10°C. The mixture is concentrated to dryness in vacuo to yield the subject compound.

EXAMPLE 18

Methoxymethyl 6-fluoro-2-methyl-4-(p-methylsulfinylphenyl)-indenyl-1-acetic acid.

Chloromethyl methyl ether (0.055 mole) is added to a suspension of 6-fluoro-2-methyl-4-(p-methylsulfinylphenyl)-indenyl-1-acetic acid (0.05 mole) and anhydrous potassium carbonate (0.15 mole) in 250 ml. of anhydrous acetone. The mixture is allowed to stir overnight at room temperature. Diethyl ether is added (about 200 ml.) and the mixture is filtered. The filtrate is washed once with 100 ml. of water and dried over anhydrous sodium sulfate. It is then filtered and the solvent is removed in vacuo. The residue is chromatographed on 200 g. of acid-washed aluminia, using ether-petroleum ether (varying from 10 to 60% ether by volume) as the eluent, to give the subject compound.

EXAMPLE 19

β-Dimethylaminomethyl 5-fluoro-2-methyl-7-(p-methylsulfinylstyrryl)-indenyl-3-acetic acid A solution of 0.0054 mole of N,N'-dicyclohexyl carbodiimide in 6 ml. of anhydrous tetrahydrofuran is added to a solution of 5-fluoro-2-methyl-7-(p-methylsulfinylstyrryl)-indenyl-3-acetic acid (0.005 mole) and 2-diethylaminoethanol (0.0054 mole) in 17 ml. of anhydrous tetrahdrofuran. The mixture is stirred at ambient temperature overnight. The dicyclohexylurea is removed by filtration and 2 ml. of glacial acetic acid is added to the filtrate. After the mixture has stood for one hour, it is filtered and 200 ml. of ether is added to the filtrate. The solution is then extracted three times with 100 ml. of 2.5 N HCl and the extracts are combined, washed twice with 100 ml. of ether, ice-cooled, made slightly alkaline with concentrated NH$_4$OH and extracted three times with 100 ml. of ether. The ether extracts are combined, washed ten times with 100 ml. of water to remove traces of starting amine, dried over anhydrous potassium carbonate, filtered and evaporated in vacuo. The oily residue is the subject compound.

When 2-dimethylaminoethanol, 3-dimethylamino-1-propanol, 3-diethylamino-1-propanol, N-β-hydroxyethylpiperidine, N-β-hydroxyethylpyrrolidine, N-hydroxymethylpyrrolidine, N-methyl-2-hydroxymethylpyrrolidine, N-ethyl-2-hydroxymethylpiperidine, 1-β-hydroxyethyl-4'-methylpiperazine or N-β-hydroxyethyl morpholine is used in the above procedure in place of 2-diethylaminoethanol, the corresponding β-dimethylaminoethyl, γ-dimethylaminopropyl, γ-diethylaminopropyl, β-N-piperidinylethyl, β-N-pyrrolidinylethyl, N-pyrrolidinylmethyl, α'-(1'-methylpyrrolidinylmethyl), 4-methyl-1-piperazinylethyl, N-ethyl-2-piperidinylethyl and N-morpholinylethyl esters are obtained.

EXAMPLE 20

Ethyl 5-fluoro-2-methyl-7-(p-methylsulfinylbenzyl)-indenyl-3-acetic acid

A mixture of 0.1 mole of 5-fluoro-2-methyl-7-(p-methylsulfinylbenzyl)-indenyl-3-acetic acid, 0.2 g. of p-toluenesulfonic acid, 100 ml. of absolute ethanol and 75 ml. of dry benzene is refluxed on a steam bath while slowly distilling the solvent. After 17 hours the residual solvent is removed under reduced pressure. The residue is slurried in aqueous bicarbonate and then with water until neutral. The resulting ethyl ester is recrystallized from ethyl acetate.

Similarly, when methanol, propanol, t-butanol or benzyl alcohol are used in place of ethanol in the above example, there is obtained the corresponding ester.

EXAMPLE 21

5-Fluoro-2-methyl-7-(p-methylsulfinylphenethyl)-indenyl-3-acetic acid

A mixture of 25, 100 or 500 parts of 5-fluoro-2-methyl-7-(p-methylsulfinylphenethyl)-indenyl-3-acetic acid and 25 parts of lactose is granulated with suitable water, and to this is added 100 parts of maize starch. The mass is passed through a 16 mesh screen. The granules are dried at a temperature below 60°C. The dry granules are passed through a 16 mesh screen and mixed with 3.8 parts of magnesium stearate. They are then compressed into tablets suitable for oral administration.

EXAMPLE 22

6-Fluoro-2-methyl-4-(p-methylsulfinylphenyl)-indenyl-1-acetic acid

A mixture of 50 parts of 6-fluoro-2-methyl-4-(p-methylsulfinylphenyl)-indenyl-1-acetic acid, 3 parts of the calcium salt of lignin sulphonic acid and 237 parts of water is ball-milled until the size of substantially all of the particles of the sulfone is less than 10 microns. The suspension is diluted with a solution containing 3 parts of sodium carboxymethyl cellulose and 0.9 parts of the butyl ester of p-hydroxy benzoic acid in 300 parts of water. There is thus obtained an aqueous suspension suitable for oral administration for therapeutic purposes.

What is claimed is:

1. A compound of the formula:

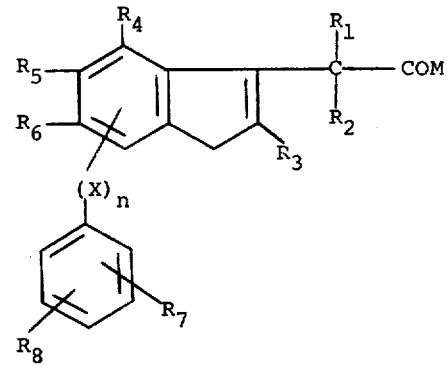

wherein
$R_1$, $R_2$, $R_4$, and $R_6$ are each hydrogen;
$R_3$ is $C_{1-5}$alkyl;
$R_5$ is hydrogen, halo, $C_{1-5}$dialkylamino, $C_{2-5}$alkanoyloxy, $C_{2-5}$alkenyl, $C_{2-5}$alkenyloxy, $C_{1-5}$alkoxy, $C_{1-5}$alkylthio, benzyloxy, $C_{1-5}$alkylsulfinyl or $C_{1-5}$alkyl;
$R_7$ is hydrogen;
$R_8$ is hydrogen, $C_{1-5}$alkylthio or $C_{1-5}$alkylsulfinyl;
n is 1;
X is $C_{2-5}$alkenylene; and
M is hydroxy, $C_{1-5}$alkoxy or β-D-glucopyranosiduronyl.

2. The compound of claim 1 wherein M is hydroxy and X is vinylene.

3. The compound of claim 2 wherein $R_8$ is $C_{1-5}$ alkylsulfinyl.

4. The compound of claim 3 wherein $R_3$ is methyl, $R_5$ is fluoro, $R_8$ is p-methylsulfinyl and X is in the 7-position of the indene nucleus.

* * * * *